(12) United States Patent
Petrillo, Sr.

(10) Patent No.: US 11,036,064 B1
(45) Date of Patent: Jun. 15, 2021

(54) MACULAR DEGENERATION STICK-ON-EYEGLASS FILTERS TO REDUCE GLARE AND DISTORTION

(71) Applicant: Gary Michael Petrillo, Sr., Wallingford, CT (US)

(72) Inventor: Gary Michael Petrillo, Sr., Wallingford, CT (US)

(73) Assignee: Gary Michael Petrillo, Sr., Wallingford, CT (US)

( * ) Notice: Subject to any disclaimer, the term of this patent is extended or adjusted under 35 U.S.C. 154(b) by 0 days.

(21) Appl. No.: 16/747,056

(22) Filed: Jan. 20, 2020

Related U.S. Application Data

(60) Provisional application No. 62/957,153, filed on Jan. 4, 2020.

(51) Int. Cl.
*G02C 7/10* (2006.01)
*A61F 9/02* (2006.01)
*G02C 9/00* (2006.01)

(52) U.S. Cl.
CPC .............. *G02C 7/104* (2013.01); *A61F 9/023* (2013.01); *A61F 9/025* (2013.01); *G02C 9/00* (2013.01); *G02C 2202/10* (2013.01)

(58) Field of Classification Search
CPC ............................. G02C 7/104; G02C 2202/10
See application file for complete search history.

(56) References Cited

U.S. PATENT DOCUMENTS 5,502,516 A * 3/1996 Elterman ................. G02C 7/10
351/41
5,764,333 A * 6/1998 Somsel ................. G02C 7/086
351/158
2010/0041003 A1 * 2/2010 Beville ................. G09B 19/00
434/258

FOREIGN PATENT DOCUMENTS

| BR | PI0805981-0 A2 * | 9/2010 | |
| BR | 2020170143746 U2 * | 1/2019 | |
| CN | 104306102 A * | 1/2015 | ............... A61F 9/00 |
| CN | 205972461 U * | 2/2017 | |

OTHER PUBLICATIONS

English translation of BR 202017014374 U2 (Year: 2019).*

* cited by examiner

*Primary Examiner* — Charlie Y Peng

(57) ABSTRACT

People with (AMD) Adult Macular Degeneration have great difficulty seeing, because their damaged retina sees double vision and distortion. The vision loss is a deterioration of light sensing cells of the retina. Direct or reflecting sunlight and headlights cause extreme glaring and distortion. There are magnifying binocular-fitted eyeglasses for precise detail, and an eye patch, which entirely blocks out all vision, which puts strain and pressure on the dominant eye. Not much is offered to block bright glare, distorted images and double vision associated with AMD.

Figure 1:
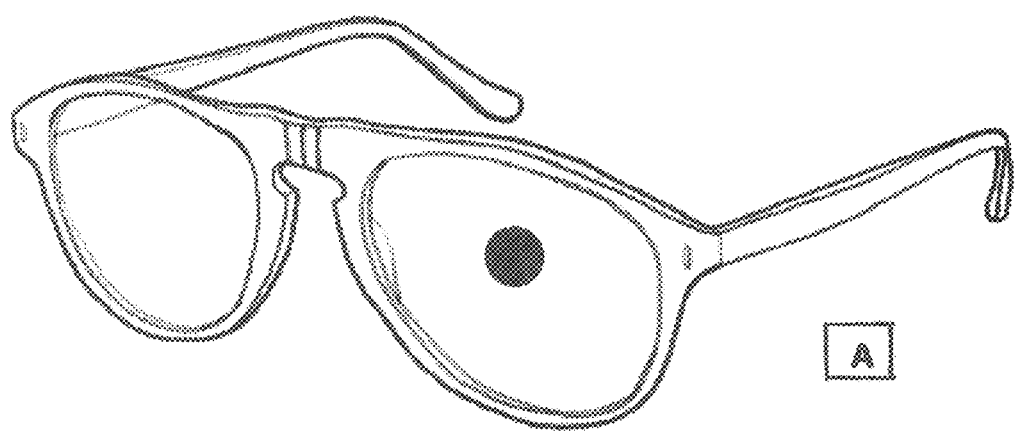
Figure 1:
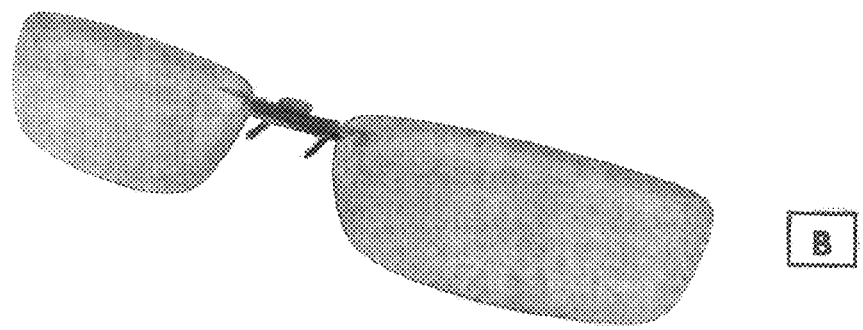
Figure 1:
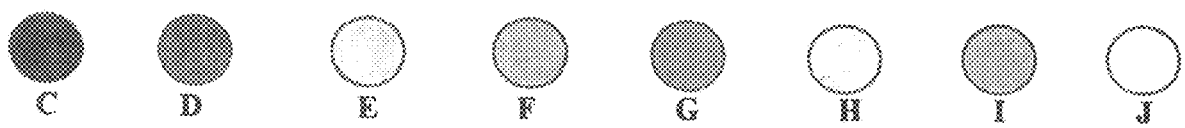

This invention enables adults and children with AMD to self-apply a stick-on eyeglass multi-colored filter UV protectant disc, placed only in front of the affected eye's pupil, on the front of the eyeglass lens. An eye patch blocks all vision completely. However, this invention is an improvement, by which the user chooses optional translucent or solid multi colored, self-applied color filter discs, having different elective properties, which blocks only the affected retina from bright sun, reflections, headlight glare, double vision and distortion, without affecting the users peripheral (side view) vision.

11 Claims, 3 Drawing Sheets

A

TYPICAL STICK-ON
FILTER
COVERS CENTRAL
EYE PUPIL ONLY

B

EYE PATCH

MACULAR DEGENERATION STICK-ON-EYEGLASS FILTERS TO REDUCE GLARE AND DISTORTION

This application claims the benefit of U.S. Provisional Allocation No. 629571531-4-2020

BACKGROUND

AMD, Adult Macular Degeneration affects a central area of the retina known as the macula, which is responsible for sharp central vision when doing everyday activities such as reading, watching television, driving and facial recognition. The vision loss affects what you see directly in the front center of your eye, but not your peripheral (side view) vision. Macular degeneration is a progressive vision deficiency resulting from deterioration of the central part of the retina, which results in changes in color perception and vision loss.

The Dry Form of AMD is when you develop small yellow deposits, called drusen, in your macula. However, when they get bigger and more abundant, they dim or distort your vision, especially when reading. As the condition gets worse, the light sensitive cells in the macula get thinner and eventually will die. In the atrophic form, you may have blind spots in the center of your vision. When it gets worse, you lose your central vision at the back of your eye. The center of your vision can become fuzzy and wavy and you experience double vision. When it worsens it may not be severe, but it can progress to the point of having symptoms, including dark spots that can block your central vision.

The Wet Form happens when blood vessels grow underneath your macula. These blood vessels will leak blood and fluid into your retina. Your vision gets distorted so that straight lines look wavy. You can have blind spots, loss of central vision and double vision. These blood vessels and their bleeding will eventually form a scar, leading to permanent loss of central vision. Having Wet or Dry AMD is accompanied by great sensitivity and distortion from glare when a person is in bright sunlight or viewing on-coming auto headlights. Even when a person is in a shaded area, sun can reflect from the water, the road, hood or chrome of a car, and glass building window fronts, etc. producing very harsh disturbing glare and distortion.

There are many eyeglasses for AMD that have strong magnifying lenses and binocular magnification for delicate precise applications. Sunglasses reduce some glare for daytime driving, but not the associated distortion and double vision with AMD, and are not suitable for driving at night or in dark tunnels.

The new intense auto LED headlights that give off an extensive blue-violet light increases retina damage. When a person with AMD looks at headlights, they don't see just a pair of on-coming lights, they see 6 or more because of the severe distortion and resembles cars passing each other into your lane. An eye patch for driving at night will prevent all glare from all auto headlights because it blocks out the entire vision of the damaged eye. It is very difficult to drive with one eye closed (day or night) because you lose your peripheral vision. The ability to navigate or perceive distance of oncoming autos, distance to traffic light and intersections, turning corners, or awareness of sidewalks, curbs and pedestrians at cross roads, are most difficult to judge.

BRIEF DESCRIPTION OF THE INVENTION

People with AMD find it most comfortable to drive just before daylight or just before dusk or, when it's cloudy out, because they may see less distortion in their damaged eye and it's bright enough to drive without on-coming headlights. There is a definite need to help people with AMD to be able to drive better without the intense glare of headlights, to be out in the bright sunshine and do normal activities and watch sports, or be able to limit distortion and wavy lines watching television or reading, and to view computer screens, without wearing a patch which blocks out total vision of the entire affected eye. Furthermore, wearing a patch is no easy task when you read, computer viewing, doing your normal daily routines, or when watching TV and theater movies because your dominant eye is always straining.

The invention gives consumers improvement and favorable support to those people with AMD to freely go about their daily routines. These self-applied stick-on-eyeglass-vinyl filter UV protectant discs adhere onto the front of your nonprescription or prescription eyeglasses directly in front of the eye pupil to block glare and distortion to the retina. Comprising of, but not limited to (8) eight adult and child size color vinyl filter UV protectant discs to reduce glare, and distortion from bright auto head lights, sun light reflective glares, double vision and distortion, whereas; the stick-on-filter disc, comprising of, but not limited to round size (10 mm) for adult and round (6 mm) for children, to cover only the central vision of the affected eye's pupil. Moreover, it means the person can reduce distortion and glare to the retina and most importantly still see peripheral vision on the side, bottom and top of their eye glasses.

BRIEF DESCRIPTION OF THE ART

FIG. 1 Pair of prescription or nonprescription eyeglasses

FIG. 1A Stick-on black filter disc on one single eyeglass lens of the affected eye FIG. 1B Clip on sunglasses FIG. 1: One round solid black, and seven round translucent lightly tinted UV protectant discs; which allow dull, misty soft light, but without detailed, glaring distortion.

(1-C): Black stick-on-filter, solid color
(1-D): Dark Grey stick-on-filter, translucent
(1-E): Light Grey stick-on filter, translucent
(1-F): Blue Tint stick-on filter, translucent
(1-G): Green Tint stick-on filter, translucent
(1-H): Rose Tint stick-on filter, translucent
(1-I): Blue Blocking stick-on filter, translucent
(1-J): Hazy clear stick-on filter, translucent They comprise of, but not limited to (8) eight adult and child sized self-applied stick-on eyeglass vinyl filter, UV protectant discs that adhere to the eyeglasses with a tacky, removable, reusable type resin to only cover the defective eye's pupil to keep the retina from seeing distortion, double vision and glare.

Figure 2:
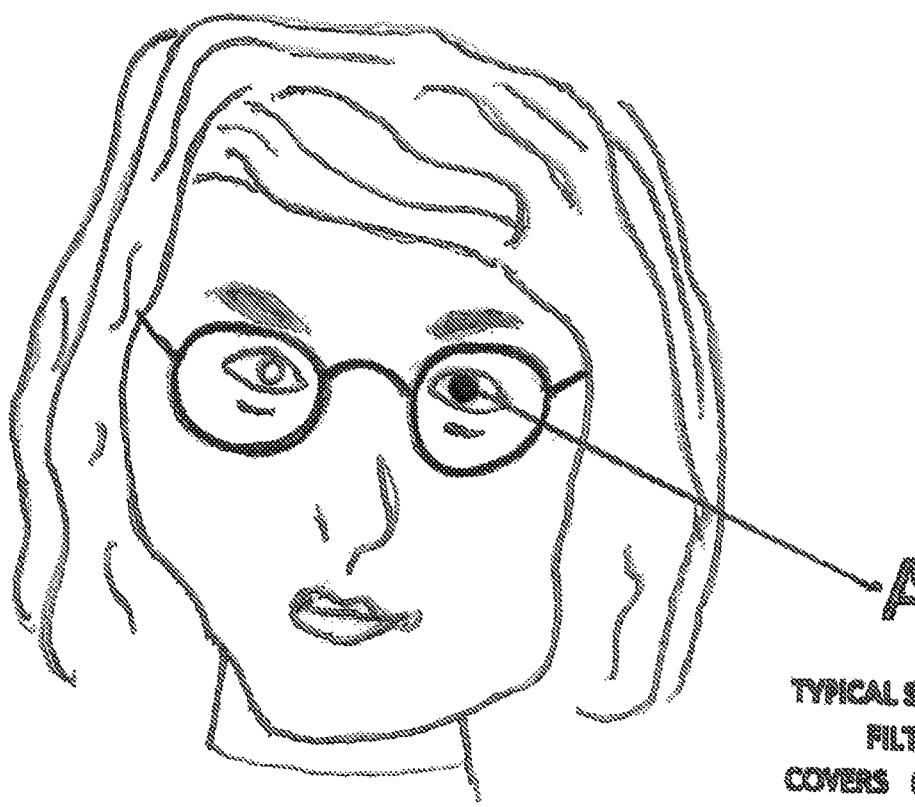
Figure 2:

FIG. 2 This depicts a person (A) wearing a pair of eyeglasses with a stick-on eyeglass glare and distortion reducing vinyl filter UV protectant disc, as well as a person (P) wearing an eye patch.

Figure 3:
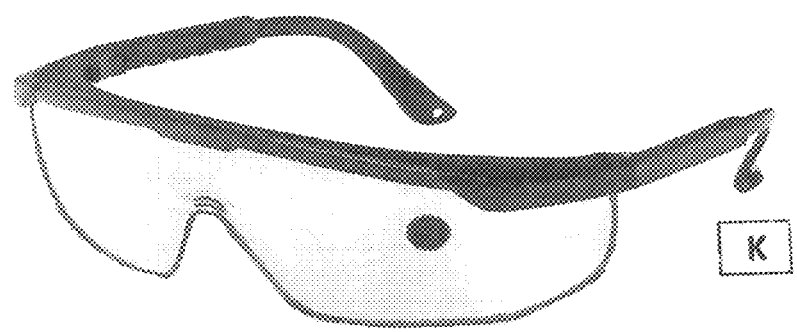
Figure 3:
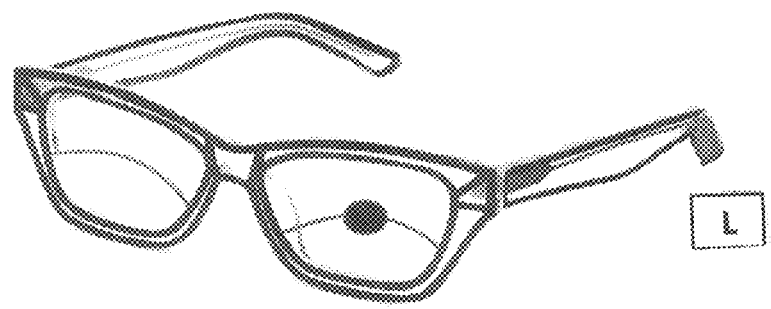
Figure 3:
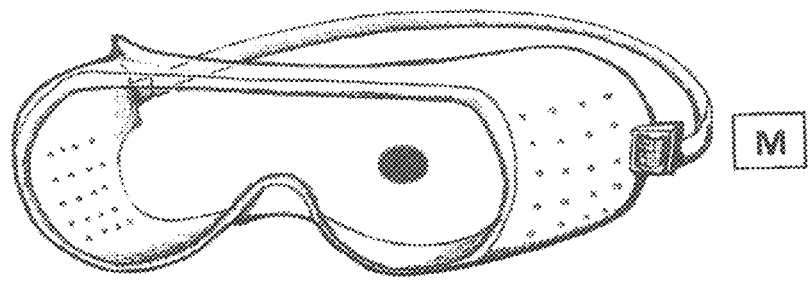

FIG. 3 Shown are: (K)-safety glasses, (L)-bifocals, and (M)-goggles with stick-on glare and distortion reducing UV protectant vinyl filter discs.

DETAILED DESCRIPTION OF SPECIFICATIONS

FIG. 1 These pair of glasses FIG. 1 resembles a prescription or nonprescription pair of eyeglasses. The stick-on-eyeglass filter FIG. 1-A (Solid Black) is shown covering only the single lens pupil. Notice that the stick-on-filter disc only blocks the small area of central vision that is causing the distortion and not the top, bottom or sides.

This means that the glare and distortion is blocked to the retina, whereas; the user can still have their peripheral (side view) vision to see all the surrounding areas such as; approaching streets, sidewalks, curbs, traffic intersections, autos, and pedestrians moving on sidewalks and cross streets far better than one eye would capture wearing a patch. Also, it is much more comfortable to drive with a small stick-on-filter in front of your pupil than wearing an eye patch, which causes complete vision loss, as well as eliminating any peripheral (side view) vision. The eyeglasses can be worn while driving, out shopping, sport events, daily routines, or anytime. The stick-on-filter reduces glare, double vision and distortion associated with AMD affected eye.

FIG. 1-B Is a clip-on pair of sunglasses which can be used over your eyeglasses to cut down on the brightness to both eyes. They can be worn right over the eyeglasses stick-on filter disc during bright sunshine days, even while you're driving, which help reduce glare to the peripheral vision in both eyes. And, if you're still driving, when it's starting to get dark, extremely cloudy or entering a tunnel, and you can't drive well with reduced light, you merely move the clip-on sunglass upwards and you have clear vision for night time driving and moreover the stick-on-fitter disc will still stop the glare and distortion of on-coming headlights to the affected eye's retina.

FIG. 1: C-D-E-F-G-H-I-J Below are seven (8) round stick-on color filter UV protectant discs. In order are: Solid Black, and seven (7) translucent, which allow incoming light to enter, but not detailed distortion or glare, are; Dark Grey, Light Gray, Blue Tint, Green Tint, Rose Tint, Blue Blocking, and Hazy Clear. Solid black is used to block out all glare and distortion from autos headlights, or bright sunshine and their reflections. Dark, Light Grey and Hazy Clear is used to resemble cloudy days or when it's not that bright out but the user is still experiencing some glare and distortion. The translucent Blue, Green, Rose tint filters can be used for a different color scheme, or to match a compatible color of their own flip-up sunglasses, but will not allow detailed distortion.

The Blue Blocking stick-on filter disc, blocks out the bright sun's harmful rays, blue-violet rays from digitized computer screens, and reflective rays from water and snow.

FIG. 2-A This is a person wearing eyeglasses with a single stick-on filter UV protectant disc over their affected left eye pupil. You can see how much peripheral (side view) vison they have all around their eye.

Also, it allows the user to have both eyes open for complete full image of what's ahead of them by tilting their head or move their eyes to look over the top, or under the bottom or the sides of the filter. They are never restricted from a whole entire view because they choose where to look. This is a much more relaxed experience than wearing an eye patch FIG. 2-P which causes complete blackout to the entire eye, while straining your dominant eye.

FIG. 3 Are (K) safety glasses, (L) bifocals, and (M) goggles. The user is not limited to what type of eye covering they can use in their daily tasks. Moreover, they have a kit that comprises of optional multi colored stick-on eyeglass discs to choose from, if their daily preference changes.

EMBODIMENTS OF THE INVENTION

The embodiments, comprising of, but not limited to, an adult size portable small hinged sealed case having (8) eight (10 mm) round, self-applied stick-on eyeglass vinyl UV protectant colored filter discs for adults as well as another portable small hinged sealed case having (8) eight (6 mm) of the same self-applied stick-on eyeglass vinyl UV protectant colored filter discs for children are: Solid Black, and the seven translucent being; Dark Grey, Light Grey, Hazy Clear, Light Blue, Green, Rose, and Blue Blocking. All the filter discs are treated with a UV coating protectant. They adhere to the eyeglass by means, consisting of, a self-applied, self-sticking, removable, reusable resin that is positioned and applied by the user to only cover their single defective eye's pupil. The small portable, hinged sealed case holds the filter discs onto a plastic laminated card to prevent the viscid resin from drying out so the user can carry it with them and interchange and reuse the filter discs to coincide with their daily requirements.

Exemplar (1)

When driving, an eye patch blocks out the entire vision of the affected eye. However, these self-applied stick-on eyeglass vinyl filter discs allow the user to block out the brightness, glare and distortion from bright headlights and sunshine, read road signage better without double vision, and still see peripheral (side view) vision all around them. They would be able to see car movements in their side mirrors and movement from pedestrians walking along the roads and sidewalks. The invention improves and reduces bright glare and distortion from headlights approaching your side and rear view mirrors, as well as SUV's and trucks in front of you with unusually high mounted glaring brake lights. Even a child passenger would benefit from the glare, distortion and double vison from the many different surroundings that occur while driving.

Exemplar (2)

When watching TV or at the movies, it becomes strenuous to both eyes because you're seeing double vision. The affected eye sees a totally distorted picture with crooked images, distorted faces, fuzziness and dark colors. The dominant eye perceives that double vision and finds it hard to focus due to distortion from the affected eye. Images will only become clear when they wear an eye patch over the affected eye. Wearing an eye patch will not cause worsening vision of the dominant eye, but it adds a lot of strain and pressure in that eye and becomes quite uncomfortable after a while. This becomes the same situation when reading or viewing a computer screen. Further, action movies and sports shows makes it even more straining. The stick-on-eyeglass vinyl filter disc makes watching the screen a lot more relaxing and less pressure on the dominant eye for adults and children because there is no distortion of any kind, while attaining peripheral (side view) vision.

Exemplar (3)

The stick-on eyeglass vinyl filter UV protectant discs adheres to many styles of eyeglasses, while you're at the beach, playing sports, reading, driving, computer viewing, winter goggles, and safety eye wear when you're doing chores or working on projects. The two (2) portable small hinged sealed cases comprising of, but not limited to, adult size being (10 mm) round and the children's (6 mm) round for the child who may have a similar central eye viewing defect like AMD, to reduce distortion in the same manner when playing, reading or school activities. It allows you to wear them under your clip-on sunglasses when you're driving to diffuse the bright sun to both eyes, and flip them up due to approaching darkness, to filter out double vison, distortion and glare from soon approaching, on-coming auto headlights.

Exemplar (4)

Two (2) easy to carry portable hinged sealed cases would contain the various different stick-on eyeglass multi colored vinyl filter UV protectant discs which the adult or child can place directly onto any eyeglass wear. Users can wear their own eyeglasses or over-the-counter non-prescription eyeglasses and have the benefit to use the self-applied stick-on vinyl filter UV protectant discs to block out glare, double vision and distortion to the single affected eye's retina. Whether you use prescription reading, driving or driving clip-on sunglasses, bifocals, or safety eyeglasses and goggles, or snow and ice goggles, this invention gives beneficial support by protecting the retina from viewing intense bright beams of light, headlights, bright sunlight, double vision, distortion, and glare that is associated with AMD Macular Degeneration Disease, and similar, single central eye vision loss defects, without complete blackout to the eye caused by an eye patch.

Summary

The (AMD) Adult Macular Degeneration Stick-On Eyeglass Vinyl Filters discs to reduce glare, double vision and distortion are used to prevent high glaring and bothersome bright light and LED headlight reflections to enter the central portion of the defective eye's pupil and to eliminate the terrible distortion accompanied with AMD and bright glaring light. Another improvement with this invention, is that the stick-on-eyeglass vinyl filter UV protectant disc will fit any type of reading glasses, driving glasses, bifocal glasses, safety glasses, sports wear glasses, winter and safety goggles, clip-on sunglasses, and children's eye wear, without performing any measurements, without any accessories or attachments, and without any exams, fittings, placements, adjustments or analysis from an eye-vision establishment.

The enhancement and improvement of this invention allows adults and children the flexibility, freedom, and options to change and swap out eight (8) different color UV protectant filter discs, for various reasons or localities, and to benefit and better suit their lifestyle throughout the day, without wearing a solid eye patch and causing undue pressure and strain to their dominant eye and be able to obtain peripheral (side view) vision.

Closure

The preceding explanation of the preferred embodiments of this invention have been described and introduced for the purpose of illustration, narration and description. It is not designed to be al-inclusive or to represent or limit the invention to the specific arrangements revealed. In view of the modifications and variations of the above representation, demonstrations, improvements and benefits this invention offers, it is intended that the scope of the invention not be restricted by the detailed description, but by the claims and the equivalents to the claims appended here.

Operational Sequence

The invention, consisting in the form of an adult and a children's portable small hinged sealed case, comprising of, but not limited to eight (8) different round colored stick-on eyeglass vinyl filter UV protectant discs that press and stick onto the single lens eyeglass of the defective eye retina with AMD Macular Degeneration or other similar eye deficiencies.

The method to install the round filter disc is beneficially simple for an adult or an older teen, is that they determine which stick-on filter to use and lightly place it onto the eyeglasses you intend to wear, directly in front of the center portion of the defective eye's, single eyeglass lens pupil until all the distortion and double vision is gone, produced by the affected retina. Then press it to stick the filter disc onto the eyeglass. When the daily routine changes, remove the filter and replace it with another that better suites your environment or preference.

Another method to locate the center of the pupil, which could be beneficial for a very young child or handicap individuals, is to place a mark on the front of the eyeglasses in the front center of their affected eye's pupil. Remove the eyeglasses and place the stick-on eyeglass vinyl filter disc over the mark.

Additionally, you can transfer that same mark to the back of the eyeglass, erase the front mark, and place the stick-on vinyl filter disc on the front lens in the center of the rear mark you made.

The method to change the color or density of the stick-on eyeglass UV protectant filter disc is to peel it off the eye wear and replace it with another filter disc of the user's choice.

The small, portable hinged sealed case that is carried with the user provides different colors and densities of the stick-on eyeglass vinyl colored filters to choose from. The eight (8) assorted round UV protectant discs, have meaningful and different purposes that enables the consumer an improvement by having more beneficial options to better adjust to changes in their daily routines, and to provide them with peripheral (side view) vision, which, unlike a patch, is an important enhancement for the consumer's life style.

What is being claimed:

1. A Macular Degeneration Stick-On-Eyeglass-Filters kit to reduce glare, double vision, distortion and blurred vision for a user who has Macular Degeneration disease in one eye, comprising: self-applied vinyl stick-on-eyeglass colored filter discs, that the user applies to the front side of their own clear or shaded single eyewear lens, directly in front of the pupil of the one eye, to block and diffuse bright, glaring and harsh light from entering the central vision of the one eye's damaged retina, when the user is viewing straight ahead; by only allowing opaque, undetailed, diffused light, to enter the damaged retina while blocking out bright glare and detail to prevent distorted and blurred vision, wherein the kit comprises eight different discs of eight vinyl filter colors: solid dense Black, translucent Dark Grey, translucent Light Grey, translucent Blue, translucent Green, translucent Rose, translucent Blue Blocking, and translucent Hazy Clear that provide different viewing options for the user; a UV protectant coating applied to each of the eight different discs to shield and prevent damaging Ultra Violet rays from entering the damaged retina, wherein the discs are round having a diameter of 10 mm for adults or 6 mm for children; a removable and reusable resin adhesive coated to one side of each of the eight different discs, to allow the user to apply the discs themselves on the front of the single eyewear lens, of the one eye, and to remove it and to reuse it; a personal, portable, carry-on credit card shaped sized plastic laminate on which the eight discs are disposed, which enables the user to peel off, use, and reattach each of eight discs whenever needed.

2. The Macular Degeneration Stick-On-Eyeglass-Filters kit in claim 1, wherein the discs are 1.5 mm in thickness.

3. The Macular Degeneration Stick-On-Eyeglass-Filters kit in claim 1, wherein the discs allows the user to remove and reuse the discs to either change option colors, based on their surroundings, or to use on another type of eyewear.

4. The Macular Degeneration Stick-On-Eyeglass-Filters kit in claim 1, wherein the plastic laminate is sized 3¼×2 inch on which the discs are held in place the adhesive for easy access.

5. The Macular Degeneration Stick-On-Eyeglass-Filters kit in claim 1, wherein the solid, dense Black color blocks all light to the single affected eye's pupil, to which eliminates all light to enter the damaged retina, and stops all distortion, double, and blurred vision of the one eye, when the user is viewing straight ahead.

6. The Macular Degeneration Stick-On-Eyeglass-Filters kit in claim 1, wherein the translucent Dark Grey, Light Grey and Hazy Clear colors are greyish tinted, offering the user a simulation of being outside on a cloudy day, at dusk or dawn, when glare and detailed distortion is less prevalent.

7. The Macular Degeneration Stick-On-Eyeglass-Filters kit in claim 1, wherein the translucent Blue Blocking color protects the damaged retina from the harmful effects of high energy Blue Light and UV rays when the user is looking directly forward at the sun or directly at the harmful Blue-Violet light emitted by digital screens, and prevents further damage of UV rays when the user if looking directly straight at the bright reflected glare off ice, snow, and reflected water Ultra Violet rays.

8. The Macular Degeneration Stick-On-Eyeglass-Filters kit in claim 1, wherein the translucent Blue, Green and Rose colors gives the user three separate color options to apply on their tinted sunglass lens, in front of the pupil of the diseased eye, to protect the retina from bright glare, detailed distortion, and double vision, when the user is viewing straight ahead.

9. The Macular Degeneration Stick-On-Eyeglass-Filters kit in claim 1, wherein, when the user is driving at night, the discs prevent the excessive, high intensity, bright glares of approaching car headlights from entering the damaged retina, which, without the glare-blocking diffusion this invention offers, is most startling for the driver to differentiate, due to high intensity distorted glare, how many actual cars are approaching them, in either their own single lane or entering in their head-on lane, when looking directly straight ahead at the glaring head lights of oncoming cars.

10. The Macular Degeneration Stick-On-Eyeglass-Filters kit in claim 1, wherein the user can apply, remove, and reapply the discs by themselves, without requiring any special tools, accessories, measurements, attachments, eye exams, preparations, assisted fittings, demonstrations, testing, analyses or teachings.

11. The Macular Degeneration Stick-On-Eyeglass-Filters kit in claim 1, wherein the discs are positioned in the front central portion of the user's single eyewear lens of the one eye, covering only the pupil, giving the user a more open and naturally relaxed feeling and exceptionally peripheral vision.

* * * * *